(12) United States Patent
Gibbs

(10) Patent No.: US 6,942,651 B2
(45) Date of Patent: Sep. 13, 2005

(54) ABSORBENT GARMENT CLOSURE SYSTEM HAVING NON-LINEAR FASTENING

(75) Inventor: Bernadette M. Gibbs, Statham, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 377 days.

(21) Appl. No.: 10/061,343

(22) Filed: Feb. 4, 2002

(65) Prior Publication Data

US 2003/0149419 A1 Aug. 7, 2003

(51) Int. Cl.⁷ ................................................ A61F 13/15
(52) U.S. Cl. ................................ 604/389; 604/385.01
(58) Field of Search ......................... 604/385.01, 386, 604/389–391

(56) References Cited

U.S. PATENT DOCUMENTS 5,057,097 A * 10/1991 Gesp ........................... 604/389
5,851,205 A * 12/1998 Hisada et al. .............. 604/390
6,454,753 B1 * 9/2002 Shimoe et al. ............. 604/391
6,743,321 B2 * 6/2004 Guralski et al. ............ 156/250

* cited by examiner

Primary Examiner—Larry I. Schwartz
Assistant Examiner—C. Lynne Anderson
(74) Attorney, Agent, or Firm—Hunton & Williams

(57) ABSTRACT

A fastener tab for use on an absorbent garment is provided. The fastener tab has a tab body with a proximal edge for locating proximate the garment, a distal edge opposite the proximal edge, a top edge adjacent the proximal edge, and a bottom edge opposite the top edge, and a fastening area for removeably fastening the tab body to the garment. The fastening area has a first edge. A first tangent line is tangent to a first portion of the first edge of the fastening area, a second tangent line is tangent to a second portion of the first edge of the fastening area, the second tangent line intersects the first tangent line, and one of the first and second tangent lines is non-parallel to a primary pull direction of the fastener tab.

32 Claims, 6 Drawing Sheets

ABSORBENT GARMENT CLOSURE SYSTEM HAVING NON-LINEAR FASTENING

FIELD OF THE INVENTION

The present invention relates generally to fastening devices for absorbent garments. More specifically, the present invention relates to a fastening device for an absorbent garment that has a non-linear fastening area.

BACKGROUND OF THE INVENTION

Traditionally, disposable absorbent garments such as infant diapers or training pants, adult incontinence products and other such products were constructed with a moisture-impervious outer backsheet, a moisture-pervious body-contacting inner topsheet, and a moisture-absorbent core sandwiched between the liner and backsheet. In typical diaper-type garments, the garment is affixed to a wearer by attaching one or more fastener tabs that extend across the wearer's hips to hold the back and front halves of the garment to one another.

Researchers have sought to improve upon fastener tabs for absorbent garments. The task of designing a universally suitable fastener tab is complicated by the fact that the fasteners are used on a great number of different wearers, all having slightly to very different body shapes and sizes. Also complicating the design of fastener tabs is the fact that the wearers typically move their bodies while the fasteners are attached, sometimes causing the tabs to become loose, uncomfortable or even unfastened. Yet another factor complicating the task of fastener tab design is the fact that the caregivers applying the tabs do so in a variety of ways that may or may not be suitable to properly affix tabs of the particular design being applied.

A number of different tab designs have been explored to provide suitable fit, comfort, leakage prevention, and other benefits. Typical fastener tabs are inelastic plastic tabs having an adhesive or hook-and-loop gripping portion. Such tabs may be attached directly to the diaper chassis or may have an elastic region interposed between the chassis and the inboard edge of the grip, such as is disclosed, for example, in U.S. Pat. No. 5,624,429 issued to Long et al., which is incorporated herein by reference in its entirety and in a manner consistent with the present invention. Other fastener tabs have been made that have an elasticized portion that extends all the way to the end of the tab, and have the grip attached directly to one side of the elastic portion at the outboard end, typically rendering that portion of the fastener tab inelastic. Such tabs are disclosed, for example, in U.S. Pat. No. 3,800,796 issued to Jacob, which is incorporated herein by reference in its entirety and in a manner consistent with the present invention.

Despite these and other efforts by absorbent garment manufacturers and others to provide suitable fastener tabs for absorbent garments, there is still a need to provide a more comfortable, better fitting, and easily applied fastener tab. These are just a few of the disadvantages of the prior art that the preferred embodiments seek to address.

SUMMARY OF THE INVENTION

It would be desirable to provide fastener tabs for absorbent garments that provide more control over the grip to allow better attachment to the garment. It would also be desirable to provide fastener tabs that have fastening areas shaped such that the elastic force produced by the tab varies at different points on the tab.

In accordance with these and other features of various embodiments of the invention, there is provided a fastener tab for an absorbent garment. The fastener tab has a tab body with a proximal edge for locating proximate the garment, a distal edge opposite the proximal edge, a top edge adjacent the proximal edge, and a bottom edge opposite the top edge. A fastening area for removeably fastening the tab body to the garment is provided. The fastening area has a first edge. A first tangent line is tangent to a first portion of the first edge of the fastening area, a second tangent line is tangent to a second portion of the first edge of the fastening area, the second tangent line intersects the first tangent line, and one of the first and second tangent lines is nonparallel to a primary pull direction of the fastener tab.

In accordance with other embodiments of the invention, there is provided a fastener tab for an absorbent garment. The fastener tab has a tab body with a proximal edge for locating proximate the garment, a distal edge opposite the proximal edge, a top edge adjacent the proximal edge, and a bottom edge opposite the top edge. A fastening area for removeably fastening the tab body to the garment is provided. The fastening area has a first edge. A first tangent line is tangent to a first portion of the first edge of the fastening area, a second tangent line is tangent to a second portion of the first edge of the fastening area, the second tangent line intersects the first tangent line, the first tangent line is non-parallel to one of the top edge and the bottom edge, and the second tangent line is non-parallel to one of the top edge and the bottom edge.

Other embodiments of the invention provide an absorbent garment having a garment chassis, an absorbent core, and a fastener tab. The fastener tab has a tab body with a proximal edge located proximate the garment, a distal edge opposite the proximal edge, a top edge adjacent the proximal edge, and a bottom edge opposite the top edge; and a fastening area for removeably fastening the tab body to the garment. The fastening area has a first edge. A first tangent line is tangent to a first portion of the first edge of the fastening area, a second tangent line is tangent to a second portion of the first edge of the fastening area, the second tangent line intersects the first tangent line, and one of the first and second tangent lines is non-parallel to a primary pull direction of the fastener tab.

Other embodiments of the invention provide an absorbent garment having a garment chassis, an absorbent core, and a fastener tab. The fastener tab has a tab body with a proximal edge located proximate the garment, a distal edge opposite the proximal edge, a top edge adjacent the proximal edge, and a bottom edge opposite the top edge; and a fastening area for removeably fastening the tab body to the garment. The fastening area has a first edge. A first tangent line is tangent to a first portion of the first edge of the fastening area, a second tangent line is tangent to a second portion of the first edge of the fastening area, the second tangent line intersects the first tangent line, the first tangent line is non-parallel to one of the top edge and the bottom edge, and the second tangent line is non-parallel to one of the top edge and the bottom edge.

Other embodiments of the invention provide a disposable absorbent garment having a main body defining a longitudinal direction and a cross direction substantially perpendicular to the longitudinal direction and a pair of fastener tabs. The fastener tabs are stretchable in the cross direction, are attached to the main body for securing the garment about a wearer, have a proximal end for attachment to the garment, a distal end opposite the proximal end and end edges connecting the proximal end to the distal end, have a width defined as that portion of the tab extending between the end edges in the longitudinal direction, and have a deadened zone positioned between the distal end and the proximal end, the deadened zone being a segment of substantially non-stretchable material positioned on the fastener tab to create differing zones of stretchability as the tabs are stretched in the cross direction.

These and other features of the invention will be readily apparent from the Detailed Description that follows, along with reference to the drawings appended hereto.

DETAILED DESCRIPTION OF THE PREFERRED EMBODIMENTS

Figure 1:
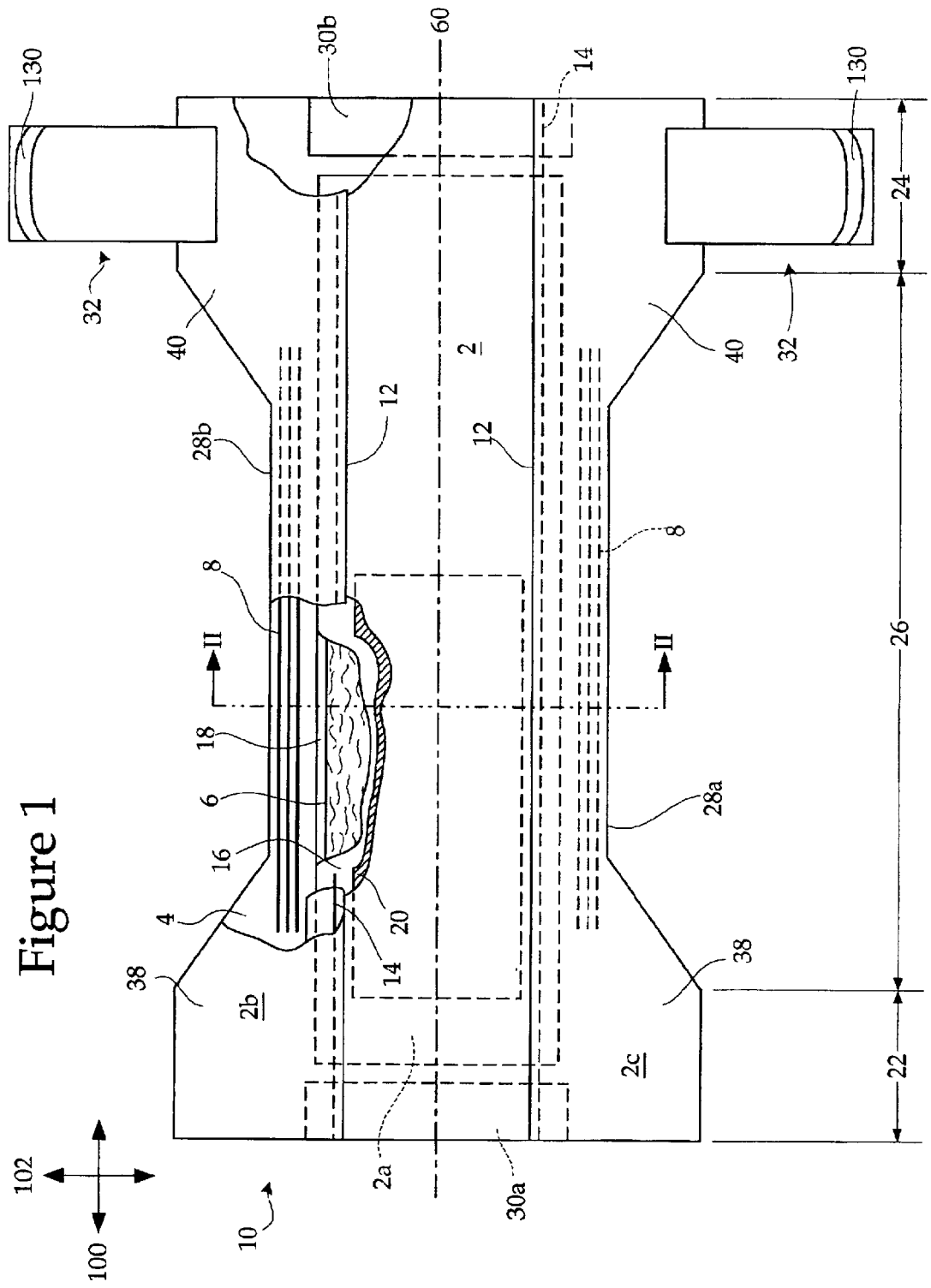
FIG. 1 is plan view of a garment in accordance with the invention.

As used herein, the term "absorbent garment" or "garment" refers to garments that absorb and contain exudates, and more specifically, refers to garments that are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. The term garment includes all variations of absorbent garments, including disposable absorbent garments that are intended to be discarded or partially discarded after a single use (i.e., they are not intended to be laundered or otherwise restored or reused) and unitary disposable absorbent garments that have essentially a single structure (i.e., do not require separate manipulative parts such as a diaper cover and insert). As used herein, the term "diaper" refers to an absorbent garment generally worn by infants and incontinent persons about the lower torso.

The invention is intended to cover all of the foregoing classes of absorbent garments, without limitation, whether disposable, unitary or otherwise. These classifications are used interchangeably throughout the specification, but are not intended to limit the invention. The invention will be understood to encompass, without limitation, all classes of absorbent garments, including those described above.

Absorbent garments and diapers may have a number of different constructions. In each of these constructions it is generally the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape, such as by fastening one or more fastener tabs. In the case of training pant-type garments and most adult incontinent products, the garment often is provided fully formed with factory-made side seams and the garment is donned by pulling it up the wearer's legs. In the case of diapers, a caregiver usually wraps the diaper around the wearer's waist and joins the side seams manually by attaching one or more fastener tabs, thereby forming a pant-like structure. For clarity, the present invention is described herein only with reference to a diaper-type garment in which the topsheet, backsheet and absorbent core are assembled into a structure that forms a pant-like garment when secured on a wearer using fastening devices, although the invention may be used with any other type of absorbent garment that may benefit from the use or addition of fastener tabs.

A preferred embodiment of the present invention comprises a disposable absorbent garment 10 of the diaper type, such as shown, for example, in FIG. 1. With reference to FIG. 1, a diaper 10 according to a preferred embodiment is shown in a relaxed condition with the effects of the elastics removed for purposes of clarity in the description. The diaper 10 chassis generally has an hourglass shape. The chassis generally can be defined in terms of a front waist region 22, a back waist region 24, and a crotch region 26. Those skilled in the art will recognize that "front" and "back" are relative terms, and these regions may be transposed without departing from the scope of the present invention. Alternatively, the diaper chassis can be configured in a generally rectangular shape or in a "T" shape. The diaper preferably comprises a topsheet 2, a backsheet 4, which may be substantially coterminous with the topsheet 2, and an absorbent core 6 disposed between at least a portion of the topsheet 2 and backsheet 4. Throughout this description, the terms "topsheet" and "backsheet" denote the relationship of these materials or layers with respect to the absorbent core 6. It is understood that additional layers may be present between the absorbent core 6 and the topsheet 2 and backsheet 4, and that additional layers and other materials may be present on the side opposite the absorbent core 6 from either the topsheet 2 or the backsheet 4. A pair of leg openings 28a, 28b extend along at least a portion of the crotch region 26 and one or more pairs of leg elastics 8 (three pairs are shown in FIG. 1) may be disposed to extend adjacent to leg openings 28a, 28b. Of course, in other embodiments, the leg elastics 8 may be omitted altogether.

The diaper 10 generally has a longitudinal direction 100 that extends generally parallel to the front-to-back axis of a wearer, and a lateral direction 102 that extends generally parallel to the side-to-side axis of a wearer. The diaper generally is symmetrical about a longitudinal centerline 60, but also may have asymmetrical components or shapes. The terms "inboard" and "outboard," as used herein, refer to positions generally along the lateral direction 102, with "inboard" locations being located closer to the longitudinal centerline 60 than "outboard" locations. "Outward" and "inward" mean in an outboard or inboard direction, respectively.

The diaper may further include a front waist elastic system 30a, a back waist elastic system 30b, and a waste containment system in the form of waste containment flaps 12 (also known as unitary leg gathers or standing leg gathers). Waste containment flaps 12 (FIG. 2) preferably extend from the front waist region 22 to the back waist region 24 along opposite sides of the longitudinal center line 60 of the diaper 10, or alternatively only along a portion thereof. The front waist region 22 and rear waist region 24 preferably include ear portions 38, 40 extending outward from the leg openings 28a, 28b to provide the garment 10 with an hourglass shape.

A variety of backsheet and topsheet constructions and materials are available and known in the art, and the invention is not intended to be limited to any specific materials or constructions of these components. The backsheet 4 may be made from any suitable pliable liquid-impervious material known in the art. Typical backsheet materials include films of polyethylene, polypropylene, polyester, nylon, and polyvinyl chloride and blends of these materials. For example, the backsheet can be comprised of a pigmented polyethylene film having a thickness in the range of 0.02–0.04 mm. The moisture-pervious topsheet 2 can be made of any suitable relatively liquid-pervious material known in the art that permits passage of liquid therethrough. Non-woven topsheet materials are exemplary because such materials readily allow the passage of liquids to the underlying absorbent core 6. Examples of suitable topsheet materials include non-woven spunbond or carded webs of polypropylene, polyethylene, nylon, polyester and blends of these materials.

The backsheet 4 and the topsheet 2 preferably are "associated" with one another. The term "associated" encompasses configurations whereby the topsheet 2 is directly joined to the backsheet 4 by affixing the topsheet 2 directly to the backsheet 4, and configurations whereby the topsheet 2 is indirectly joined to the backsheet 4 by affixing the topsheet 2 to intermediate members which in turn are affixed to the backsheet 4. While the backsheet 4 and topsheet 2 in the preferred embodiment have substantially the same dimensions, they may also have different dimensions.

In addition, the backsheet 4 may be covered with a fibrous, nonwoven fabric layer (not shown) such as is disclosed, for example, in U.S. Pat. No. 4,646,362, which is incorporated herein by reference in its entirety and in a manner consistent with the present invention. Materials for such a fibrous outer liner include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers.

The backsheet 4 may comprise multiple panels, such as three panels wherein a central poly backsheet panel is positioned adjacent the absorbent core while outboard non-woven breathable side backsheet panels are attached to the side edges of the central poly backsheet panel. The backsheet may also be formed from microporous poly coverstock for added breathability. In other embodiments, the backsheet may be a laminate of several sheets. The backsheet may further be treated to render it hydrophilic or hydrophobic, and may have one or more visual indicators associated with it, such as labels indicating the front or back of the diaper or other characters or colorations. The present invention is not limited to any particular backsheet 4 material or construction.

Figure 2:
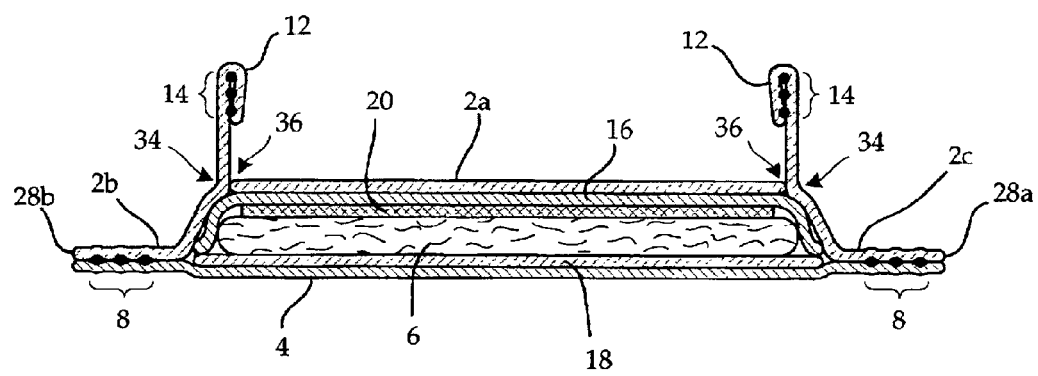
FIG. 2 is a section view along section line II—II in FIG. 1.

The topsheet 2 may be formed from one or more panels of material and may comprise a laminated sheet construction. In the embodiment of FIGS. 1 and 2, the topsheet comprises three separate portions or panels. A three-panel topsheet may comprise a central topsheet panel 2a that preferably is formed from a liquid-pervious material that is either hydrophobic or hydrophilic. The central topsheet panel 2a may be made from any number of materials, including synthetic fibers (e.g., polypropylene or polyester fibers), natural fibers (e.g., wood or cellulose), apertured plastic films, reticulated foams and porous foams to name a few. One preferred material for a central topsheet panel 2a is a cover stock of single ply non-woven material which may be made of carded fibers, either adhesively or thermally bonded, perforated plastic film, spunbonded fibers, or water entangled fibers, which generally weigh from 0.3–0.7 oz./yd$^2$ and have appropriate and effective machine direction and cross-machine direction strength suitable for use as a baby diaper cover stock material, as are known in the art. The central topsheet panel 2a preferably extends from substantially the front waist region 22 to the back waist region 24 or a portion thereof.

The second and third topsheet panels 2b, 2c in this embodiment may be positioned laterally outside of the central topsheet panel 2a. The outer topsheet panels 2b, 2c are preferably substantially liquid-impervious and hydrophobic, preferably at least in the crotch area. The outer edges of the outer topsheet panels may substantially follow the corresponding outer perimeter of the backsheet 4. The material for the outer topsheet portions or panels is preferably polypropylene and can be woven, non-woven, spunbonded, carded or the like, depending on the application.

An inner region 34 (FIG. 2) of the outer topsheet portions or panels 2b, 2c preferably are attached by, e.g., an adhesive, to the outer edges 36 of the inner topsheet portion or panel 2a. At the point of connection with the outer edges 36 of the inner topsheet portion or panel 2a, the inner regions 34 of the outer topsheet portions or panels 2b, 2c extend upwardly to form waste containment flaps 12. The waste containment flaps 12 may be formed of the same material as the outer topsheet portions or panels 2b, 2c, as in the embodiment shown. The waste containment flaps 12 may also be formed from separate elasticized strips of material that are associated with the topsheet, backsheet or both, or otherwise integrated into the garment.

The waste containment flaps 12 may be treated with a suitable surfactant to modify their hydrophobicity/hydrophilicity or imbued with skin wellness products as desired. The central topsheet portion or panel 2a may extend past the connection point with the waste containment flaps 12 and even extend to the periphery of the backsheet. Still further, the central topsheet portion or panel 2a could extend fully between the outer topsheet portions or panels 2b, 2c, and even beyond, so that the outer edges 36 of the central topsheet portion or panel 2a are coextensive with and sandwiched between the outer topsheet portions or panels 2b, 2c and the backsheet 4.

Each waste containment flap 12 preferably includes a portion that folds over onto itself to form an enclosure. One or more elastic members 14 (FIG. 2) may be secured in the enclosure in a stretched condition. When the flap elastic 14 attempts to assume the relaxed, unstretched condition, the waste containment flaps 12 rise above the surface of the central topsheet portion or panel 2a. Various other configurations of topsheets 2 and waste containment systems, such as flaps 12, are known in the art, and the present invention is not intended to be limited to any particular design for these components.

The waist elastics 30a, 30b may be similar or different structures to impart similar or different elastic characteristics to the front and back waist portions 22, 24 of the diaper. In general, the waist elastics may comprise elastically extensible foam strips positioned at the front and back waist sections 22, 24. The foam strips preferably are about 0.50 inches to about 1.50 inches wide and about 3 inches to about 6 inches long. The foam strips preferably are positioned between the topsheet portions or panels and the backsheet 4. Alternatively, a plurality of elastic strands may be employed as waist elastics rather than foam strips. The foam strips preferably are polyurethane, but could be any other suitable material that preferably decreases waist band roll over, reduces leakage from the waist ends of the absorbent garment, and generally improves comfort and fit. The front and back waist foam strips 30a, 30b preferably are stretched to about 150% to about 250% of their unstretched length (in the lateral direction 102), and preferably to about 200% of their unstretched length, before being adhesively secured between the backsheet 4 and topsheet 2. Waist elastics are known in the art, and the present invention is not limited to the use of a particular waist elastic system, or to the inclusion of waist elastics at all.

Each leg opening 28a, 28b may be provided with a leg elastic containment system 8, sometimes referred to as conventional leg gathers. In a preferred embodiment, three strands of elastic threads are positioned to extend adjacent each leg openings 28a, 28b between the outer topsheet portions or panels 2b, 2c and the backsheet 4. The selection of appropriate elastics and the construction of leg elastic containment systems is known in the art. For example, the leg elastics 8 may be ultrasonically bonded, heat/pressure sealed using a variety of bonding patterns, or glued to the diaper 10.

Various commercially available materials may be used for the leg elastics 8 and elastic members 14, such as natural rubber, butyl rubber or other synthetic rubber, urethane, elastomeric materials such as spandex, which is marketed under various names, including LYCRA (DuPont), GLOSPAN (Globe) and SYSTEM 7000 (Fulflex), and so on. The present invention is not limited to any particular elastic material or to any particular shape, size or number of elastics.

The underlying structure beneath the topsheet 2 may include, depending on the diaper construction, various combinations of elements, but in each embodiment, it is contemplated that the absorbent garment preferably will include an absorbent core 6. Although the absorbent core 6 depicted in FIG. 1 has a substantially rectangular shape as viewed in the plan view, other shapes may be used, such as a "T" shape or an hourglass shape. The absorbent core 6 may extend into either or both of the front and back waist regions 24, 22. The shape and construction of the absorbent core 6 may be selected to provide the greatest absorbency in target areas where body fluids are most likely to strike the diaper 10, which is often referred to as zoned absorbency. The absorbent core 6 may also comprise a number of layers of similar or different construction. The absorbent core may be associated with the topsheet 2, backsheet 4, or any other suitable part of the garment 10 by any method known in the art, in order to fix the absorbent core 6 in place.

Generally, in a preferred embodiment, the absorbent core 6 comprises particles of superabsorbent material (SAP) distributed within a fibrous structure. Additional fibrous or particulate additives may be disposed within the absorbent core 6 to add to the core's strength and SAP efficiency or to otherwise enhance the performance of the garment. The absorbent core 6 may be partially or wholly surrounded by a tissue layer 16, 18, and other additional layers 20 may be added to provide further benefits. For example, an additional layer 20 may be disposed between the topsheet 2 and absorbent core 6, as shown in FIG. 2, and/or other additional layers may be disposed between these layers, or between absorbent core 6 and backsheet 4. The additional layer 20 or layers may comprise any useful layer known in the art or developed hereafter, such as a fluid acquisition layer, a distribution layer, an additional fibrous layer optionally containing superabsorbent particles (SAP), a wicking layer, a storage layer, or combinations and fragments of these layers. Such layers may be provided to assist with transferring fluids to the absorbent core 6, handling fluid surges, preventing rewet, containing absorbent material, improving core stability, or for other purposes. Skilled artisans are familiar with the various additional layers that may be included in absorbent articles, and the present invention is not intended to be limited to any particular type of materials used for those layers. Rather, the invention encompasses all types of wicking layers, all types of distribution layers, etc., to the extent that type of layer 20 is utilized.

The dimensions of the additional layer(s) 20 may be the same as or different from the dimensions of the absorbent core 6 and/or topsheet 2 and backsheet 4. It may be desirable to make the additional layers 20 smaller than the absorbent core 6 and located only where they are most needed, as such additional layers 20 may be relatively expensive.

The absorbent core 6 may be made from any absorbent material or materials, or combinations of such materials, known in the art or hereafter discovered. In one embodiment of the invention, the absorbent core 16 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 6 comprises a combination of a porous fibrous web and superabsorbent particles. Absorbent cores are known in the art and exemplary cores are disclosed, for example, in U.S. Pat. No. 5,281,207 issued to Chmielewski et al., U.S. Pat. No. 4,610,678 issued to Weisman et. al., U.S. Pat. No. 5,137,537 issued to Herron et. al., U.S. Pat. No. 5,147,345 issued to Young et. al., U.S. Pat. No. 6,068,620 issued to Chmielewski, and U.S. Statutory Invention Registration No. H1,565, all of which are incorporated herein by reference in their entirety, and in a manner consistent with the present invention.

Preferably, the absorbent core is thin in order to improve the comfort and appearance of a garment. The absorbent core 6 preferably comprises a tissue wrapping that at least partially encloses the fibrous structure and SAP, such as disclosed in U.S. Pat. No. 6,068,620. The tissue wrapping is useful, for example, for containing the SAP within the absorbent core 6 and providing strength to the core during manufacturing and use. In a preferred embodiment, the tissue wrapping comprises first and second tissue layers 16, 18 that encase the absorbent core 6, and may optionally also encase one or more additional layers 20. Preferably, the first tissue layer 16 is located generally between the topsheet 2 and the absorbent core 6, and is hydrophilic and fluid pervious. It is also preferred that the second tissue layer 18 be located between the backsheet 4 and the absorbent core 6 and be hydrophobic and fluid impervious. The tissue wrapping may also comprise a single tissue layer that has been folded to encase the absorbent core, and that may be zone treated to render the portion that forms the lower tissue layer 18 hydrophobic and fluid impervious. The tissue layers 16, 18 or the whole core 6 may be crimped, folded, sealed or bonded to further help contain the fibrous structure and SAP particles.

The diaper 10 is fastened onto a wearer by using one or more, and preferably two, fastener tabs 32. The fastener tabs 32 preferably are affixed to the chassis of the diaper 10 to extend laterally outward (i.e., in the lateral direction 102) from a waist region 22, 24 of the garment. The fastener tabs 32 preferably are positioned to extend outward from the ear portions 40 of the rear waist region 24, but the fastener tabs 32 may also be attached to extend outward from the front waist region 22, or from both waist regions. The fastener tabs 32 may extend from one, but preferably both, lateral sides of the diaper 10. The fastener tabs 32 may be attached to any part of the diaper chassis, such as the topsheet 2, backsheet 4, outer covering or other layer of the diaper. The fastener tabs 32 may also be attached to either side of the diaper's chassis, to multiple layers of the chassis, or may be sandwiched between the various sheets comprising the chassis of the diaper 10. Variations on the number, location, and attachment configuration of the fastener tabs 32 will be apparent to those skilled in the art based on the teachings herein, and all such variations are within the scope of the present invention.

The fastener tabs 32 of the present invention are preferably elasticized and have fastener areas 130 of particular shapes. The fastener tabs 32 may comprise any structure that is elastically extensible provided they may be joined to the diaper 10 and a fastener area to adequately handle the usage loads. The terms "elastic," "elastically extensible," and variations of these terms as used herein, are understood by those skilled in the art, and generally refer to the ability of a material or combination of materials (such as an aggregate or laminate), to be extended and retracted with little or no plastic deformation, yielding or rupturing (except as explained elsewhere) of the various parts of the material or combination of materials. The term "inelastic" and variations thereof as used herein, are understood by those skilled in the art, and generally refer to the substantial absence of elastic properties. Other meanings of these terms will be clear to those skilled in the art of absorbent garment construction.

In a preferred embodiment, the fastener tabs 32 comprise elastic laminates having one or more elastic layers bonded to one another or to one or more inelastic layers. A preferred elastic laminate comprises an elastic layer disposed between a pair of inelastic layers. The elastic layer preferably comprises a styrene based elastic film, such as those disclosed in U.S. Pat. No. 6,313,372 issued to Suzuki, which is incorporated herein by reference in its entirety and in a manner consistent with the present invention, however the elastic may also be another type of elastic film, a multidirectional elastic aggregate such as elastic webbing, netting, or scrim elastic, foam, strands or bands of suitable elastic materials, such as natural or synthetic rubber, urethane elastomers, spandex, LYCRA and elastic polymers. Other suitable elastics will be apparent to those skilled in the art in light of the present teachings. The elastic layer for an elastic laminate typically is stretched then affixed between a pair of inelastic layers, which then contract when the elastic layer contracts. In some cases, however, the elastic layer may be affixed between the inelastic layers while in a relaxed state, such as when the elastic layer is a heat-activated material that elastically contracts after being heated. The inelastic outer layers preferably comprise a nonwoven material, such as a spunbonded polypropylene or polyethylene nonwoven similar to those used for the topsheet 2, but may also be any suitable material that encases the elastic layer, protects the elastic layer, allows slideable contact between the fastener tabs 32 and other parts of the diaper 10, or prevents such sliding, protects the wearer from uncomfortable exposure to the elastic layer or provides other benefits. Other uses for the outer layer or layers will be apparent to those skilled in the art based on the teachings herein. In a preferred embodiment, the fastener tabs 32 are breathable to provide additional comfort to the wearer, i.e., the fastener tabs have a moisture vapor transmission rate (MVTR) of at least 250 grams/($m^2$24 hours), and more preferably an MVTR of about 750 grams/($m^2$24 hours), and most preferably an MVTR of about 1500 grams/($m^2$24 hours). The measurement of moisture vapor transmission rate is explained in U.S. Pat. No. 5,879,34 to Odorzynski, which is incorporated by reference herein in its entirety and in a manner consistent with the present invention. Preferred elastic laminates that are suitable for use with the present invention are FABRIFLEX 204 and FABRIFLEX 304 available from Tredegar Film Products of Richmond, Va.

The bonding between the various layers of a preferred elastic laminate preferably is accomplished using a number of heat bonds or ultrasonic bonds, but may also be accomplished using adhesives, combinations of different bonding methods, or any other joining method known in the art or later developed. The construction of such elastic laminates is known in the art, and a skilled artisan will be able to provide a suitable elastic laminate or other elastic design for the fastener tabs 32 without undue experimentation, based on the teachings provided herein.

Fastener tabs 32 may also be a "zero strain" stretch-laminate, which generally is manufactured by attaching a sheet of elastic to outer layers while the elastic is in a relaxed state, then "activating" the laminate by extending the elastic to create plastic deformation, yielding or rupturing in the outer layers. After the initial activation, the zero-strain stretch laminate behaves generally like any other elastic laminate. Such elastics are disclosed, for example, in U.S. Pat. No. 5,464,401 issued to Hasse et al., and U.S. Pat. No. 6,313,372 issued to Suzuki, which are incorporated herein by reference in their entirety and in a manner consistent with the present invention. Fastener tabs 32 may also comprise sheets, ribbons, scrims, strands, foams or other types of elastic material that may or may not be secured between outer sheets. Still another material that may be used for fastener tabs 32 is a coextruded sheet of elastic and inelastic polymers, such as is disclosed, for example, in U.S. Pat. No. 4,787,897 issued to Torimae et al., which is incorporated herein by reference in its entirety and in a manner consistent with the present invention.

Figure 3:
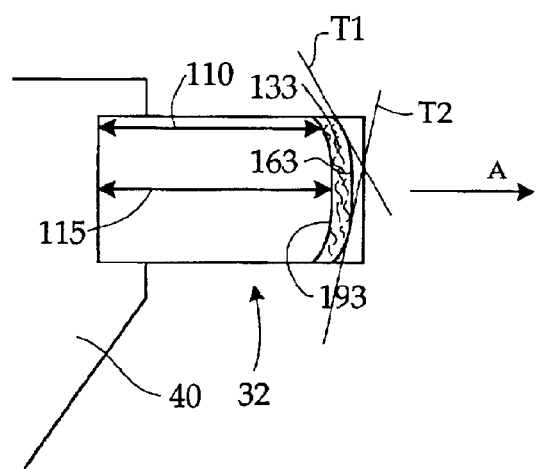
FIG. 3 is a plan view of a fastener tab in accordance with the invention.

FIGS. 3–15 show several different fastener areas 133–145 in accordance with the invention. The fastener areas can, for example, be a hook portion or a loop portion of a hook and loop fastener, or can be any other appropriate fastener such as, for example, an adhesive fastener. The embodiments shown are examples of fastener areas having an edge that is non-linear. As shown in FIG. 3, fastener area 133 has a first edge 163 that is non-linear and has at least a portion of first edge 163 that is not parallel to a primary pull direction "A" of fastener tab 32. In the example shown in FIG. 3, a second edge 193 is substantially parallel to edge 163. However, in other embodiments, the edges are not parallel. Further, either one or both of the edges (such as edges 163, 193 and FIG. 3) can be non-linear.

By making one or both of the edges non-linear, the force exerted by the fastener tab can be varied across the width (top to bottom in FIG. 3) of the tab. This difference in force is created by stretching different length portions of an elastic laminate having a uniform cross sectional area and a uniform modulus of elasticity a set distance. For example, segment 110 of tab 32 may, for example, have an at-rest length of 2 inches and segment 115 near the center of the fastener tab may, for example, have an at-rest length of 2.25 inches. If the entire fastener tab is stretched, for example, one inch to the right in FIG. 3, segment 110 will be stretched to a total length of 3 inches while segment 115 is stretched to a total length of 3.25 inches. In this example, segment 110 will be stretched to 150 percent of its at-rest length while segment 115 will be stretched to 144 percent of its at-rest length. Because segment 110 is stretched by a greater percentage of its at-rest length, the force exerted by segment 110 is greater than that exerted by segment 115. By applying the teachings of this example to the design of the fastener area, many desired elastic force distributions can be provided.

A preferred shape of a non-linear edge of a fastener tab in accordance with the invention can be described with relation to two tangent lines. FIG. 3 shows two lines tangent to first edge 163. A first tangent line T1 is tangent to first edge 163 near the upper portion of tab 32. A second tangent line T2 is tangent to first edge 163 near the lower portion of tab 32. Tangent lines T1, T2 intersect and neither of them is parallel to primary pull direction A. In other embodiments, either T1 or T2 is parallel to primary pull direction A. In some embodiments, the same two-tangent-line criteria applies to second edge 193 instead of, or as well as, first edge 163.

Figure 4:
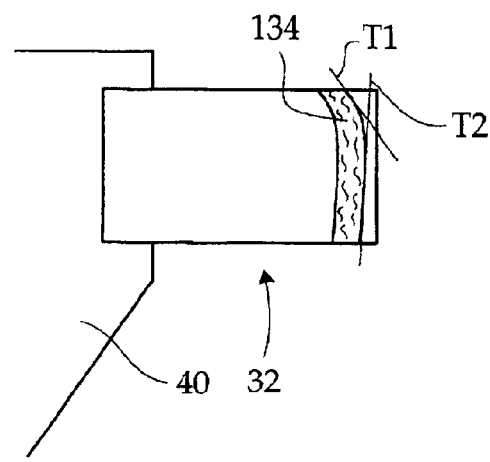
FIG. 4 is a plan view of a fastener tab in accordance with the invention.

FIGS. 3–15 show some examples of fastener tabs in accordance with the invention. These examples are in no way limiting and are just examples of some of the possible embodiments of the invention. FIG. 4 shows a fastener tab 32 having a fastener area 134 which is curved toward the diaper 10 at top edge of the fastener tab 32. Such a design provides an even elastic force in the lower and middle regions of the fastener tab 32 and a greater elastic force in the upper region of fastener tab 32. This embodiment provides the diaper with a tighter waist fit as compared to the leg fit.

Figure 5:
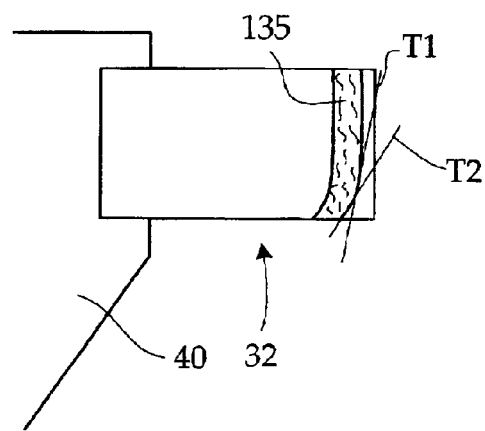
FIG. 5 is a plan view of a fastener tab in accordance with the invention.
Figure 6:
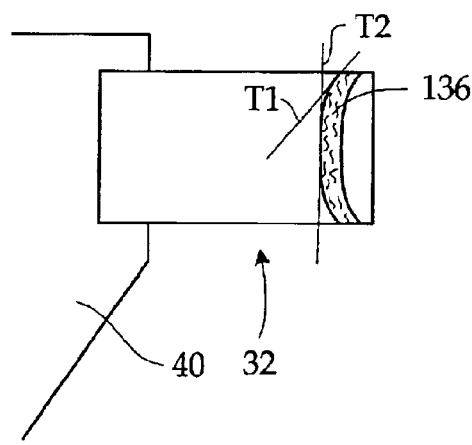
FIG. 6 is a plan view of a fastener tab in accordance with the invention.

FIG. 5 shows a fastener tab 32 having a fastener area 135 which provides a greater elastic force in the lower portion of fastener tab 32 than in the middle and upper portions of fastener tab 32. This embodiment provides a tighter leg fit relative to the waist fit. FIG. 6 shows a fastener tab 32 having a fastener area 136 that provides a greater elastic force in the central region of fastener tab 132 compared to the upper and lower regions of fastener tab 32. By providing less elastic force in the upper and lower regions of fastener tab 32, rolling or curling of the upper and lower edges of fastener tab 32 can be reduced or eliminated.

Figure 7:
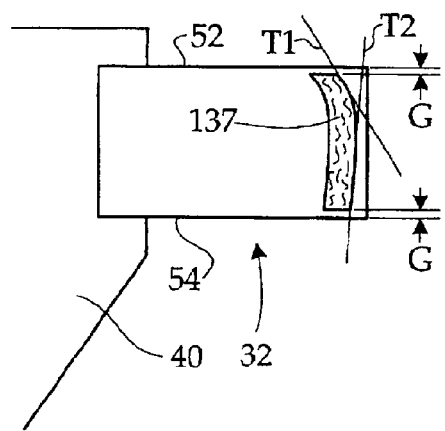
FIG. 7 is a plan view of a fastener tab in accordance with the invention.
Figure 8:
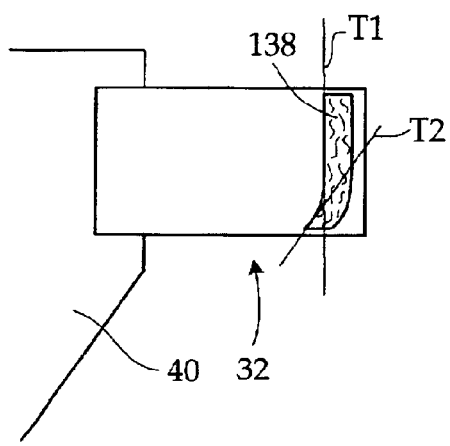
FIG. 8 is a plan view of a fastener tab in accordance with the invention.
Figure 9:
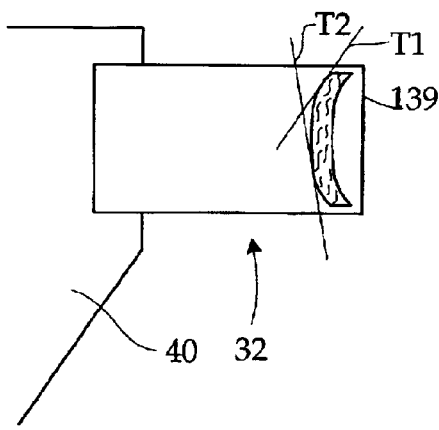
FIG. 9 is a plan view of a fastener tab in accordance with the invention.

FIGS. 7–9 show embodiments that are similar to the embodiments shown in FIGS. 4–6 respectively, except that the embodiments shown in FIGS. 7–9 have fastener areas 137–139 that do not extend to the upper and lower edges 52, 54 of the fastener tab. A gap G is formed between at least one of, and preferably both, the upper and lower edges 52, 54 of the fastener tab. By not extending the fastener area to the upper and lower edges 52, 54 of the fastener tab, the possibility of irritation resulting from the fastener area coming in contact with the wearer is reduced.

Figure 10:
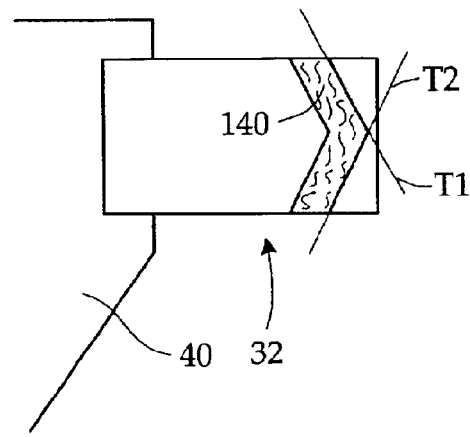
FIG. 10 is a plan view of a fastener tab in accordance with the invention.
Figure 11:
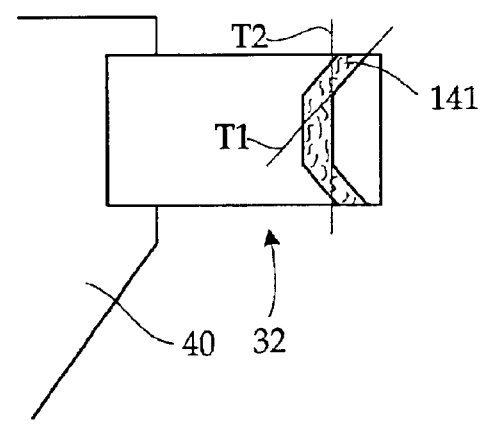
FIG. 11 is a plan view of a fastener tab in accordance with the invention.
Figure 12:
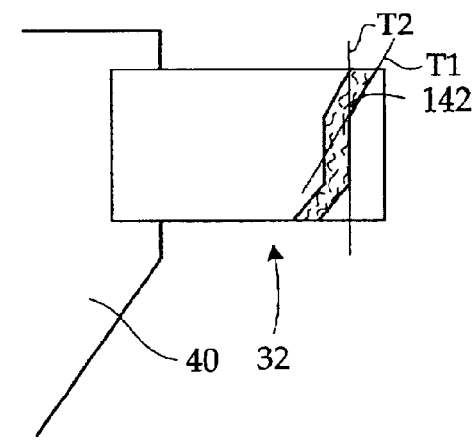
FIG. 12 is a plan view of a fastener tab in accordance with the invention.
Figure 13:
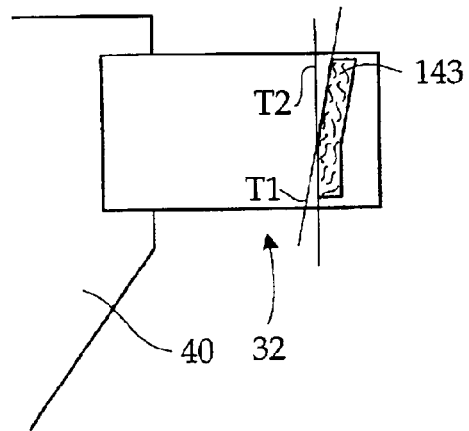
FIG. 13 is a plan view of a fastener tab in accordance with the invention.
Figure 14:
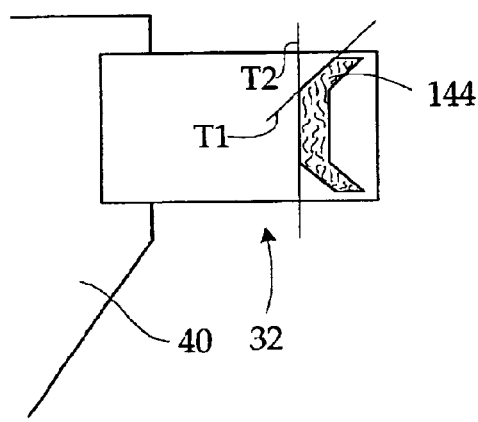
FIG. 14 is a plan view of a fastener tab in accordance with the invention.

While FIGS. 3–9 show embodiments in which the fastener area has a curved edge, other embodiments have non-linear edges that are made up of only linear components. For example, FIG. 10 shows a fastener tab having a fastener area 140 that provides a greater elastic force at the upper and lower edges of fastener tab 32, a minimum elastic force at the center of fastener tab 32, and an elastic force that gradually increases with distance from the center of the tab toward either the upper or lower edge of the tab. FIGS. 11–14 show other examples of fastener tabs having fastener areas 141–144, respectively, that have non-linear edges made up of linear components.

Figure 15:
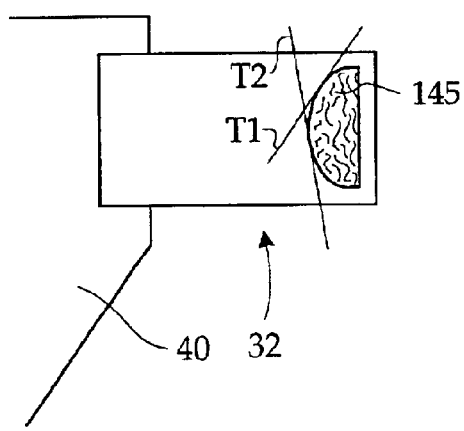
FIG. 15 is a plan view of a fastener tab in accordance with the invention.

While FIGS. 3–14 show embodiments in which the fastener areas have substantially parallel opposite edges, other embodiments have opposite edges that are not parallel. For example, FIG. 15 shows a fastener tab 32 having a fastener area 145 with a curved edge opposite a straight edge. This embodiment provides a greater fastening strength in the central portion of the fastener area 145 because more fastener material exists in that portion. This increased fastener area can be helpful in restraining the greater elastic force created in the central region of the fastener tab by the circular shape of the edge closest to the diaper.

Other embodiments, uses, and advantages of the invention will be apparent to those skilled in the art from consideration of the specification and practice of the invention disclosed herein. The specification should be considered exemplary only.

I claim:

1. A fastener tab for use on an absorbent garment, the fastener tab comprising:
   a tab body having a proximal edge for locating proximate the garment, a distal edge opposite the proximal edge, a top edge adjacent the proximal edge, and a bottom edge opposite the top edge; and
   a fastening area for removeably fastening the tab body to the garment, the fastening area having a first edge,
      wherein a first tangent line is tangent to a first portion of the first edge of the fastening area,
      a second tangent line is tangent to a second portion of the first edge of the fastening area,
      the second tangent line intersects the first tangent line, and
      one of the first and second tangent lines is non-parallel to a primary pull direction of the fastener tab, and
   the fastening area having a second edge,
      wherein the second edge is substantially parallel to the first edge along the entire length of the second edge.

2. The tab of claim 1, wherein a portion of the tab body is elastic.

3. The tab of claim 2, wherein the first portion of the first edge is curved.

4. The tab of claim 3, wherein the first portion of the first edge is concave toward the proximal edge of the tab.

5. The tab of claim 3, wherein the first portion of the first edge is convex toward the proximal edge of the tab.

6. The tab of claim 3, wherein the second portion of the first edge is curved.

7. The tab of claim 6, wherein the first and second portions of the first edge are concave toward the proximal edge of the tab.

8. The tab of claim 6, wherein the first and second portions of the first edge are convex toward the proximal edge of the tab.

9. The tab of claim 3, wherein the second portion of the first edge is straight.

10. The tab of claim 2, wherein the first portion of the first edge is straight.

11. The tab of claim 10, wherein the second portion of the first edge is straight.

12. A fastener tab for use on an absorbent garment, the fastener tab comprising:
a tab body having a proximal edge for locating proximate the garment, a distal edge opposite the proximal edge, a top edge adjacent the proximal edge, and a bottom edge opposite the top edge; and
a fastening area for removeably fastening the tab body to the garment, the fastening area having a first edge,
wherein a first tangent line is tangent to a first portion of the first edge of the fastening area,
a second tangent line is tangent to a second portion of the first edge of the fastening area,
the second tangent line intersects the first tangent line,
the first tangent line is non-parallel to one of the top edge and the bottom edge, and
the second tangent line is non-parallel to one of the top edge and the bottom edge, and
the fastening area having a second edge,
wherein the second edge is substantially parallel to the first edge along the entire length of the second edge.

13. An absorbent garment, comprising:
a garment chassis;
an absorbent core; and
a fastener tab, the fastener tab having
a tab body with a proximal edge located proximate the garment, a distal edge opposite the proximal edge, a top edge adjacent the proximal edge, and a bottom edge opposite the top edge; and
a fastening area for removeably fastening the tab body to the garment, the fastening area having a first edge,
wherein a first tangent line is tangent to a first portion of the first edge of the fastening area,
a second tangent line is tangent to a second portion of the first edge of the fastening area,
the second tangent line intersects the first tangent line, and
one of the first and second tangent lines is non-parallel to a primary pull direction of the fastener tab, and
the fastening area having a second edge,
wherein the second edge is substantially parallel to the first edge along the entire length of the second edge.

14. The garment of claim 13, wherein a portion of the tab body is elastic.

15. The garment of claim 14, wherein the first portion of the first edge is curved.

16. The garment of claim 15, wherein the first portion of the first edge is concave toward the proximal edge of the tab.

17. The garment of claim 15, wherein the first portion of the first edge is convex toward the proximal edge of the tab.

18. The garment of claim 15, wherein the second portion of the first edge is curved.

19. The garment of claim 18, wherein the first and second portions of the first edge are concave toward the proximal edge of the tab.

20. The garment of claim 18, wherein the first and second portions of the first edge are convex toward the proximal edge of the tab.

21. The garment of claim 15, wherein the second portion of the first edge is straight.

22. The garment of claim 14, wherein the first portion of the first edge is straight.

23. The garment of claim 22, wherein the second portion of the first edge is straight.

24. The garment of claim 13, wherein the first edge stops short of the top edge of the tab body.

25. The garment of claim 13, wherein the first edge stops short of the bottom edge of the tab body.

26. The garment of claim 25, wherein the first edge stops short of the top edge of the tab body.

27. An absorbent garment, comprising:
a garment chassis;
an absorbent core; and
a fastener tab, the fastener tab having
a tab body with a proximal edge located proximate the garment, a distal edge opposite the proximal edge, a top edge adjacent the proximal edge, and a bottom edge opposite the top edge; and
a fastening area for removeably fastening the tab body to the garment, the fastening area having a first edge,
wherein a first tangent line is tangent to a first portion of the first edge of the fastening area,
a second tangent line is tangent to a second portion of the first edge of the fastening area,
the second tangent line intersects the first tangent line,
the first tangent line is non-parallel to one of the top edge and the bottom edge, and
the second tangent line is non-parallel to one of the top edge and the bottom edge, and
the fastening area having a second edge,
wherein the second edge is substantially parallel to the first edge along the entire length of the second edge.

28. A disposable absorbent garment comprising:
a main body defining a longitudinal direction and a cross direction substantially perpendicular to the longitudinal direction; and
a pair of fastener tabs, the fastener tabs
being stretchable in the cross direction,
attached to the main body for securing the garment about a wearer,
having a proximal end for attachment to the garment, a distal end opposite the proximal end and end edges connecting the proximal end to the distal end,
having a width defined as that portion of the tab extending between the end edges in the longitudinal direction, and
having a deadened zone positioned between the distal end and the proximal end, the deadened zone being a segment of substantially non-stretchable material positioned on the fastener tab to create differing zones of stretchability as the tabs are stretched in the cross direction,
the deadened zone having a first edge extending across at least a portion of the width of the tab, the first edge being non-parallel to the fastener tab proximal end, and the deadened zone having a second edge,
wherein the second edge is substantially parallel to the first edge along the entire length of the second edge.

29. The garment of claim 28, wherein the deadened zone is created by a segment of hook and loop material extending across the width of the tab non-linearly.

30. The garment of claim 29 28, wherein the deadened zone is created by hook and loop material attached to the fastener tabs.

31. The garment of claim 28, wherein the deadened zone is created by a segment of hook and loop material extending across the width of the tab, and
at least a portion of the deadened zone is linear.

32. The garment of claim 31, wherein the deadened zone is created by hook and loop material attached to the fastener tabs.

* * * * *